(12) United States Patent
Marshall

(10) Patent No.: US 8,380,530 B2
(45) Date of Patent: Feb. 19, 2013

(54) PERSONALIZED HEALTH RECORDS WITH ASSOCIATIVE RELATIONSHIPS

(75) Inventor: Philip Marshall, Portland, OR (US)

(73) Assignee: WEBMD LLC., New York, NY (US)

( * ) Notice: Subject to any disclaimer, the term of this patent is extended or adjusted under 35 U.S.C. 154(b) by 732 days.

(21) Appl. No.: 12/025,421

(22) Filed: Feb. 4, 2008

(65) Prior Publication Data

US 2008/0215367 A1 Sep. 4, 2008

Related U.S. Application Data

(60) Provisional application No. 60/899,234, filed on Feb. 2, 2007.

(51) Int. Cl.
G06Q 10/00 (2006.01)
G06Q 50/00 (2006.01)

(52) U.S. Cl. .................. 705/2; 705/3; 707/802

(58) Field of Classification Search .................. 705/2–3; 707/802
See application file for complete search history.

(56) References Cited

U.S. PATENT DOCUMENTS

| | | |
|---|---|---|
| 4,315,309 A | 2/1982 | Coli |
| 4,622,013 A | 11/1986 | Cerchio |
| 4,766,542 A | 8/1988 | Pilarczyk |
| 4,812,994 A | 3/1989 | Taylor et al. |
| 4,839,822 A | 6/1989 | Dormond et al. |
| 4,847,764 A | 7/1989 | Halvorson |
| 4,858,121 A | 8/1989 | Barber et al. |
| 4,868,376 A | 9/1989 | Lessin et al. |
| 4,882,474 A | 11/1989 | Anderl et al. |
| 4,916,611 A | 4/1990 | Doyle, Jr. et al. |
| 4,949,251 A | 8/1990 | Griffin et al. |
| 4,960,982 A | 10/1990 | Takahira |
| 4,984,272 A | 1/1991 | McLlroy et al. |
| 5,072,383 A | 12/1991 | Brimm et al. |
| 5,077,666 A | 12/1991 | Brimm et al. |
| 5,093,911 A | 3/1992 | Parks et al. |
| 5,103,498 A | 4/1992 | Lanier et al. |
| 5,136,716 A | 8/1992 | Harvey et al. |
| 5,150,409 A | 9/1992 | Elsner |
| 5,239,617 A | 8/1993 | Gardner et al. |

(Continued)

FOREIGN PATENT DOCUMENTS

| | | |
|---|---|---|
| WO | WO-9512812 A1 | 5/1995 |
| WO | WO-0185021 A1 | 11/2001 |

OTHER PUBLICATIONS

Ananda, A. et al., "Distributed Computing Systems: Concepts and Structures", Table of Contents only (IEEE Computer Society Press 1991). 4 pages.

(Continued)

*Primary Examiner* — Luke Gilligan
(74) *Attorney, Agent, or Firm* — Wilmer Cutler Pickering Hale & Dorr LLP.

(57) ABSTRACT

A method for processing a personal health record (PHR) which includes a plurality of events each having a time stamp. The method includes creating a plurality of event-concept pairs by mapping each of the plurality of events in the PHR to a corresponding health concept, assigning to each of the plurality of event-concept pairs the time stamp of the event corresponding to the event-concept pair, identifying associations among the plurality of event-concept pairs, identifying an associative subset of event-concept pairs among the plurality of event-concept pairs, and linking a plurality of members of the associative subset of event-concept pairs to form a thread, in which the thread presents a relationship among the plurality of members of the associative subset of event-concept pairs.

28 Claims, 11 Drawing Sheets

U.S. PATENT DOCUMENTS

| | | |
|---|---|---|
| 5,241,671 A | 8/1993 | Reed et al. |
| 5,251,152 A | 10/1993 | Notess |
| 5,267,155 A | 11/1993 | Buchanan et al. |
| 5,277,188 A | 1/1994 | Selker |
| 5,291,399 A | 3/1994 | Chaco |
| 5,299,121 A | 3/1994 | Brill et al. |
| 5,301,105 A | 4/1994 | Cummings, Jr. |
| 5,301,246 A | 4/1994 | Archibald et al. |
| 5,301,319 A | 4/1994 | Thurman et al. |
| 5,317,507 A | 5/1994 | Gallant |
| 5,317,742 A | 5/1994 | Bapat |
| 5,324,718 A | 6/1994 | Loftsson |
| 5,325,294 A | 6/1994 | Keene |
| 5,325,478 A | 6/1994 | Shelton et al. |
| 5,327,341 A | 7/1994 | Whalen et al. |
| 5,337,919 A | 8/1994 | Spaulding et al. |
| 5,408,619 A | 4/1995 | Oran |
| 5,410,704 A | 4/1995 | Norden-Paul et al. |
| 5,426,747 A | 6/1995 | Weinreb et al. |
| 5,430,875 A | 7/1995 | Ma |
| 5,459,536 A | 10/1995 | Shalon et al. |
| 5,465,082 A | 11/1995 | Chaco |
| 5,468,110 A | 11/1995 | McDonald et al. |
| 5,471,382 A | 11/1995 | Tallman et al. |
| 5,472,954 A | 12/1995 | Loftsson |
| 5,477,447 A | 12/1995 | Luciw et al. |
| 5,479,523 A | 12/1995 | Gaborski et al. |
| 5,485,544 A | 1/1996 | Nonaka et al. |
| 5,491,800 A | 2/1996 | Goldsmith et al. |
| 5,502,944 A | 4/1996 | Kraft et al. |
| 5,517,405 A | 5/1996 | McAndrew et al. |
| 5,519,607 A | 5/1996 | Tawil |
| 5,542,420 A | 8/1996 | Goldman et al. |
| 5,546,472 A | 8/1996 | Levin |
| 5,550,971 A | 8/1996 | Brunner et al. |
| 5,558,638 A | 9/1996 | Evers et al. |
| 5,559,885 A | 9/1996 | Drexler et al. |
| 5,559,888 A | 9/1996 | Jain et al. |
| 5,560,005 A | 9/1996 | Hoover et al. |
| 5,560,008 A | 9/1996 | Johnson et al. |
| 5,560,011 A | 9/1996 | Uyama |
| 5,572,422 A | 11/1996 | Nematbakhsh et al. |
| 5,576,954 A | 11/1996 | Driscoll |
| 5,583,831 A | 12/1996 | Churchill et al. |
| 5,588,148 A | 12/1996 | Landis et al. |
| 5,590,038 A | 12/1996 | Pitroda |
| 5,593,267 A | 1/1997 | McDonald et al. |
| 5,594,786 A | 1/1997 | Chaco et al. |
| 5,596,994 A | 1/1997 | Bro |
| 5,597,995 A | 1/1997 | Williams et al. |
| 5,612,869 A | 3/1997 | Letzt et al. |
| 5,613,106 A | 3/1997 | Thurman et al. |
| 5,619,709 A | 4/1997 | Caid et al. |
| 5,619,991 A | 4/1997 | Sloane |
| 5,623,242 A | 4/1997 | Dawson, Jr. et al. |
| 5,625,767 A | 4/1997 | Bartell et al. |
| 5,629,981 A | 5/1997 | Nerlikar |
| 5,633,368 A | 5/1997 | Hirsenkorn |
| 5,664,109 A | 9/1997 | Johnson et al. |
| 5,664,207 A | 9/1997 | Crumpler et al. |
| 5,666,492 A | 9/1997 | Rhodes et al. |
| 5,671,282 A | 9/1997 | Wolff et al. |
| 5,671,362 A | 9/1997 | Cowe et al. |
| 5,672,154 A | 9/1997 | Sillen et al. |
| 5,682,142 A | 10/1997 | Loosmore et al. |
| 5,689,229 A | 11/1997 | Chaco et al. |
| 5,689,247 A | 11/1997 | Welner |
| 5,692,125 A | 11/1997 | Schloss et al. |
| 5,694,806 A | 12/1997 | Martin et al. |
| 5,696,877 A | 12/1997 | Iso |
| 5,700,998 A | 12/1997 | Palti |
| 5,704,044 A | 12/1997 | Tarter et al. |
| 5,704,371 A | 1/1998 | Shepard |
| 5,710,551 A | 1/1998 | Ridgeway |
| 5,713,485 A | 2/1998 | Liff et al. |
| 5,724,575 A | 3/1998 | Hoover et al. |
| 5,735,105 A | 4/1998 | Stroud et al. |
| 5,736,580 A | 4/1998 | Huntington et al. |
| 5,737,396 A | 4/1998 | Garcia |
| 5,737,539 A | 4/1998 | Edelson et al. |
| 5,742,816 A | 4/1998 | Barr et al. |
| 5,745,366 A | 4/1998 | Higham et al. |
| 5,754,111 A | 5/1998 | Garcia |
| 5,758,095 A | 5/1998 | Albaum et al. |
| 5,764,923 A | 6/1998 | Tallman et al. |
| 5,772,585 A | 6/1998 | Lavin et al. |
| 5,776,783 A | 7/1998 | Kell |
| 5,778,225 A | 7/1998 | Supernaw-Issen et al. |
| 5,781,442 A | 7/1998 | Engleson et al. |
| 5,784,635 A | 7/1998 | McCallum |
| 5,790,409 A | 8/1998 | Fedor et al. |
| 5,790,785 A | 8/1998 | Klug et al. |
| 5,794,178 A | 8/1998 | Caid et al. |
| 5,797,515 A | 8/1998 | Liff et al. |
| 5,799,292 A | 8/1998 | Hekmatpour |
| 5,799,981 A | 9/1998 | Tung et al. |
| 5,803,498 A | 9/1998 | Tung et al. |
| 5,805,454 A | 9/1998 | Valerino, Sr. et al. |
| 5,805,676 A | 9/1998 | Martino |
| 5,809,476 A | 9/1998 | Ryan |
| 5,812,410 A | 9/1998 | Lion et al. |
| 5,815,665 A | 9/1998 | Teper et al. |
| 5,822,544 A | 10/1998 | Chaco et al. |
| 5,823,948 A | 10/1998 | Ross, Jr. et al. |
| 5,823,949 A | 10/1998 | Goltra |
| 5,827,180 A | 10/1998 | Goodman |
| 5,832,449 A | 11/1998 | Cunningham |
| 5,832,450 A | 11/1998 | Myers et al. |
| 5,832,488 A | 11/1998 | Eberhardt |
| 5,833,599 A | 11/1998 | Schrier et al. |
| 5,835,758 A | 11/1998 | Nochur et al. |
| 5,835,897 A | 11/1998 | Dang |
| 5,835,900 A | 11/1998 | Fagg, III et al. |
| 5,836,312 A | 11/1998 | Moore |
| 5,841,970 A | 11/1998 | Tabuki |
| 5,845,255 A | 12/1998 | Mayaud |
| 5,845,264 A | 12/1998 | Nellhaus |
| 5,848,397 A | 12/1998 | Marsh et al. |
| 5,852,820 A | 12/1998 | Burrows |
| 5,857,179 A | 1/1999 | Vaithyanathan et al. |
| 5,857,190 A | 1/1999 | Brown |
| 5,862,327 A | 1/1999 | Kwang et al. |
| 5,864,855 A | 1/1999 | Ruocco et al. |
| 5,867,821 A | 2/1999 | Ballantyne et al. |
| 5,903,889 A | 5/1999 | de la Huerga et al. |
| 5,905,884 A | 5/1999 | Williams |
| 5,915,240 A | 6/1999 | Karpf |
| 5,926,811 A | 7/1999 | Miller et al. |
| 5,937,387 A | 8/1999 | Summerell et al. |
| 5,950,630 A | 9/1999 | Portwood et al. |
| 5,953,704 A | 9/1999 | McIlroy et al. |
| 5,960,403 A | 9/1999 | Brown |
| 5,966,715 A | 10/1999 | Sweeney et al. |
| 5,967,789 A | 10/1999 | Segel et al. |
| 5,974,412 A | 10/1999 | Hazlehurst et al. |
| 5,978,842 A | 11/1999 | Noble et al. |
| 6,003,020 A | 12/1999 | Hazlehurst et al. |
| 6,006,269 A | 12/1999 | Phaal |
| 6,018,619 A | 1/2000 | Allard et al. |
| 6,031,818 A | 2/2000 | Lo et al. |
| 6,047,327 A | 4/2000 | Tso et al. |
| 6,070,160 A | 5/2000 | Geary |
| 6,073,106 A | 6/2000 | Rozen et al. |
| 6,073,163 A | 6/2000 | Clark et al. |
| 6,076,166 A | 6/2000 | Moshfeghi et al. |
| 6,092,196 A | 7/2000 | Reiche |
| 6,112,183 A | 8/2000 | Swanson et al. |
| 6,132,218 A | 10/2000 | Benja-Athon |
| 6,141,759 A | 10/2000 | Braddy |
| 6,167,523 A | 12/2000 | Strong |
| 6,178,416 B1 | 1/2001 | Thompson et al. |
| 6,189,036 B1 | 2/2001 | Kao |
| 6,219,674 B1 | 4/2001 | Classen |
| 6,253,228 B1 | 6/2001 | Ferris et al. |
| 6,263,330 B1 | 7/2001 | Bessette |
| 6,270,456 B1 | 8/2001 | Iliff |
| 6,289,353 B1 | 9/2001 | Hazlehurst et al. |

| | | |
|---|---|---|
| 6,292,796 B1 | 9/2001 | Drucker et al. |
| 6,334,778 B1 | 1/2002 | Brown |
| 6,347,374 B1 | 2/2002 | Drake et al. |
| 6,362,836 B1 | 3/2002 | Shaw et al. |
| 6,366,956 B1 | 4/2002 | Krishnan |
| 6,385,611 B1 | 5/2002 | Cardona |
| 6,401,072 B1 | 6/2002 | Haudenschild et al. |
| 6,449,598 B1 | 9/2002 | Green et al. |
| 6,505,196 B2 | 1/2003 | Drucker et al. |
| 6,532,459 B1 | 3/2003 | Berson |
| 6,581,038 B1 | 6/2003 | Mahran |
| 6,584,445 B2 | 6/2003 | Papageorge |
| 6,738,754 B1 | 5/2004 | Norman, Jr. |
| 6,767,325 B2 | 7/2004 | Iliff |
| 6,826,696 B1 | 11/2004 | Chawla et al. |
| 6,904,408 B1 | 6/2005 | McCarthy et al. |
| 7,020,618 B1 | 3/2006 | Ward |
| 7,069,226 B1 | 6/2006 | Kleinfelter |
| 7,149,456 B2 | 12/2006 | Yamagata |
| 7,149,756 B1 | 12/2006 | Schmitt et al. |
| 7,464,021 B1 | 12/2008 | Myers et al. |
| 7,512,575 B2 | 3/2009 | Mahesh |
| 7,725,331 B2 | 5/2010 | Schurenberg et al. |
| 7,805,320 B2 * | 9/2010 | Deitsch et al. ............ 705/3 |
| 7,860,729 B2 * | 12/2010 | Stangel .................. 705/2 |
| 8,122,012 B2 * | 2/2012 | Dettinger et al. ......... 707/722 |
| 2001/0021910 A1 | 9/2001 | Goldstein |
| 2002/0165737 A1 | 11/2002 | Mahran |
| 2003/0212579 A1 | 11/2003 | Brown et al. |
| 2004/0044548 A1 | 3/2004 | Marshall et al. |
| 2004/0122790 A1 | 6/2004 | Walker et al. |
| 2006/0004607 A1 | 1/2006 | Marshall et al. |
| 2006/0167992 A1 | 7/2006 | Cheung et al. |
| 2006/0265249 A1 * | 11/2006 | Follis et al. ............. 705/3 |
| 2008/0033985 A1 * | 2/2008 | Aronow et al. ........... 707/102 |
| 2010/0094658 A1 * | 4/2010 | Mok et al. ............... 705/3 |

OTHER PUBLICATIONS

Annual Review of Information Science and Technology, vol. 25, Edited by Martha E. Williams, University of Illinois, published by the American Society for Information Science, 1990. 4 pages.

Anonymous, Apr. 16, 2001, New Product Newswire, Drug Topics; Oradell, Medical Economics Inc., vol. 145, Issue 8, pp. 74-77.

Brazier et al., "Distributed Open Systems", Table of Contents only (IEEE Computer Society Press 1994). 7 pages.

Caid et al, Context Vector-Based Text Retrieval, Aug. 1997. 11 pages.

Carenini, et al., "An Information-Based Bayesian Approach to History Taking," 5th Conf. on Artificial Intelligence in Medicine Europe, pp. 129-138, Jun. 1995.

Carpenter et al, The ART of Adaptive Pattern Recognition by a Self-Organizing Neural Network, Boston University, IEEE 1988. 27 pages.

Casavant et al., "Readings in Distributed Computing Systems", Table of Contents only (IEEE Computer Society Press 1994). 4 pages.

Chen, Machine Learning for Information Retrieval: Neural Networks, Symbolic Learning, and Genetic Algorithms, Journal of the American Society for Information Science, 46(3):194-216, 1995.

Cheriton et al., "Decentralizing a Global Naming Service for Improved Performance and Fault Tolerance", ACM Trans. Computer Systems, vol. 7, No. 2, May 1989, pp. 147-183.

Day et al., "Programming Methodology Group Memo 79: References to Remote Mobile Objects in Thor", Dec. 1993. 11 pages.

Detmer, W. et al., MedWeaver: Integrating Decision Support, Literature Searching, and Web Exploration using the UMLS Metathesaurus (1997). 5 pages.

Frakes et al., Information Retrieval, Data Structures & Algorithms, Software Engineering Guild and University of Chile, 1992. Accessed via the Internet on Jun. 5, 2012. 391 pages.

Frisch et al., "Automated Telephone Interviewing to Improve Health Care Access," Proc. Twelfth Int'l. Symp. on the Creation of Electronic Health Record System and Global Conf. on Patient Cards, vol. 2, pp. 529-535, May. 1996.

Hurson, A. et al., "Multidatabase Systems: An Advanced Solution for Global Information Sharing", Table of Contents only (IEEE Computer Society Press 1994). 7 pages.

Jia et al., "Highly Concurrent Directory Management in the Galaxy Distributed System", Proc. 10th Int'l Conf. Distributed Computing Systems, IEEE Computer Society Press, 1990, pp. 416-423.

Joseph et al., "Object-Oriented Databases: Design and Implementation", Proceedings of the IEEE, vol. 79, No. 1, Jan. 1991, pp. 42-64.

Kohonen, The Self-Organizing Map, Senior Member, IEEE, Proceedings of the IEEE, vol. 78, No. 9, Sep. 1990. 17 pages.

Liskov et al., "Programming Methodology Group Memo 77: Distributed Object Management in Thor", Jun. 1993. 17 pages.

Miller Freeman, Mar. 31, 2001, What to do When a Pharmacist Suspects a Script is Forged, Pulse, London; Issue 486000, pp. 76.

Nahouraii et al., "Object-Oriented Databases", Table of Contents only (IEEE Computer Society Press 1991). 4 pages.

Ozsu et al., "Distributed Data Management: Unsolved Problems and New Issues" (published in T. Casavant et al., Readings in Distributed Computing Systems (IEEE Comp. Soc. Press 1994). 35 pages.

PR Newswire, WellMed Introduces Industry's First Comprehensive Personal Health Management System Including Online Health Record, Aug. 23, 1999. 3 pages.

Press Release, Feb. 22, 1999. Apelon, Inc. "WellMed and Lexical Technology Announce Joint Development Agreement for Online Consumer Health Records". 2 pages.

Quintana, Y. Intelligent Medical Information Filtering, International Journal of Medical Informatics, 1998. 14 pages.

Quintana, Y. User Modeling Information Filtering for Consumer Information, New Media Lab, IEEE 1997. 4 pages.

Rumelhart et al., Parallel Distributed Processing, Explorations in the Microstructure of Cognition, vol. 1: Foundations, PDP Research Group, The Massachusetts Institute of Technology, 1986. Chapters 4, 9-11. 132 pages.

Salton, Automatic Text Processing, The Transformation, Analysis, and Retrieval of Information by Computer, Cornell University, 1989. Chapters 5, 8-12. 269 pages.

Sasseen et al., Convectis: A Context Vector-Based On-Line Indexing System, Aug. 1997. 7 pages.

Sasseen et al., Docuverse: A Context Vector-Based Approach to Graphical Representation of Information Content, Aug. 1997. 12 pages.

Singhal et al., "The Architectural Overview of the Galaxy Distributed Operating System" (published in T. Casavant et al., Readings in Distributed Computing Systems (IEEE Comp. Soc. Press 1994). 21 pages.

Videotape, Barbara Liskov, "Thor: An Object-Oriented Database System," The Distinguished Lecture Series VII (Nov. 29, 1993).

* cited by examiner

200

| CLINICAL MEDICAL TERM OR TERMS | LAY MEDICAL TERM | CUI |
|---|---|---|
| GUARDING OF THE ABDOMEN-INVOLUNTARY | ABDOMEN SENSITIVE TO TOUCH | C0238547 |
| NIPPLE DISCHARGE, ABNORMAL | ABNORMAL NIPPLE DISCHARGE | 00149741 |
| ADRENALIN-TEST | ADRENALIN LEVEL | C0201998 |
| AMINOPHYLLINE, SERUM | AMINOPHYLLINE LEVEL | C0002575 |
| AMITRIPTYLINE, SERUM | AMITRIPTYLINE LEVEL | C0202316 |
| AMMONIA -- TEST | AMMONIA LEVEL | 00201879 |
| SALICYLATE, SERUM | ASPIRIN LEVEL | 00202463 |
| CONGENITAL BAND SYNDROME | BABY BANDS | C0220724 |
| URINATION, BED WETTING | BED WETTING | 00014394 |
| OROPHARYNX LESION BIOPSY | BIOPSY OF THROAT | 00192211 |
| PERIODS, MENSTRUAL – BLEEDING BETWEEN | BLEEDING BETWEEN MENSTRUAL PERIODS | 00302811 |
| EAR DISCHARGES/BLEEDING | BLEEDING FROM EAR | 00271412 |
| HOG (QUALITATIVE – SERUM) | BLOOD HCG LEVEL | 00430064 |
| HEMOGLOBIN, SERUM | BLOOD HEMOGLOBIN LEVEL | 00523685 |
| LEAD – SERUM | BLOOD LEAD LEVEL | 00524167 |
| LITHIUM, SERUM | BLOOD LITHIUM LEVEL | 00337452 |
| BORN WITH AN OPTIC DISC ABNORMALITY | BORN WITH AN ABNORMAL OPTIC NERVE | 00521571 |
| TACHYPENEA | BREATHING FAST | C0231835 |
| BACKBONE FRACTURE | BROKEN BACK | 00080179 |
| METACARPAL FRACTURE | BROKEN METACARPAL | 00272677 |
| SACRUM/COCCYX FRACTURE | BROKEN TAILBONE | 00149860 |
| MONOPLEGIA OF LOWER EXTREMITY | CAN'T MOVE LEG | 00154702 |
| DYSURIA | PAIN WITH URINATION | 00028961 |
| VISION, NIGHT BLINDNESS | CAN'T SEE AT NIGHT | 00028077 |
| INABILITY TO SLEEP | CAN'T SLEEP | 00021603 |
| SMELL, IMPAIRED | CAN'T SMELL | 00481703 |
| MEDIAN NERVE RELEASE | CARPAL TUNNEL SURGERY | C0196576 |
| HOARSENESS OR CHANGING VOICE | CHANGING VOICE | 00518179 |
| CHEST LACERATION | CHEST CUT | C0432951 |
| HICCUPS, CHRONIC | CHRONIC HICCUPS | 00019521 |
| CHRONIC PAIN AND FATIGUE CONDITION | CHRONIC PAIN | 00150055 |
| DIURETIC | WATER PILL | C0033231 |
| HYDROXZINE INJECTION | CORTISONE SHOT | C0010137 |
| COMPUTERIZED TOMOGRAPHY OF ORBIT | CT OF EYE SOCKET | 00202754 |
| CXR | CHEST XRAY | 00202783 |
| FRACTURE | BROKEN | 00016658 |
| DIABETES MELLITUS | SUGAR DISEASE | 00011849 |

| ID | Association type | Associated category pairs |
|----|---|---|
| 1 | Is_a (taxonomic or parent-child association) | disease-disease, medication-medication, etc. (any two identical categories) |
| 2 | Is_treatment_for | treatment-disease |
| 3 | Is_test_for | test-disease, test-symptom, test-diagnosis |
| 4 | Is_symptom_of | symptom-disease |
| 5 | Is_related_anatomy | anatomicPart-disease |
| 6 | Is_Benefit_related_to | benefit-treatment, benefit-medication |
| 7 | Is_risk_factor_for | risk_factor-medication, risk_factor-treatment |
| 8 | Is_a_side_effect_of | side_effect-medication, side_effect-treatment |
| 9 | Is_related_to | disease-disease |
| 10 | Is_caused_by | riskFactor-disease |
| 11 | Is_prevented_by | symptom-medication, symptom-treatment, disease-medication, disease-treatment |
| 12 | Is_contraindicated_in | medication-disease |
| 13 | Interacts_with | medication-medication |

FIG. 3

PERSONALIZED HEALTH RECORDS WITH ASSOCIATIVE RELATIONSHIPS

This application is a Non-Prov of Prov (35 USC 119(e)) application 60/899,234 filed on Feb. 2, 2007.

FIELD OF THE INVENTION

Background of the Invention

The breadth of medical knowledge has grown to a level that even health professionals can hardly remember and use all information relevant to their specialty. In addition, this information is growing so quickly that any individual will have difficulty staying up to date. For example, health issues are addressed in ever-increasing tens of thousands of online sites, with potentially millions of pages of health related information. Also, a significant portion of medical information is stored in many searchable databases available to health professionals.

A different type of medical information exists in the clinical data collected as personal health records of individuals. Each personal record may include multiple items of different types including conditions, symptoms, diagnoses, test results, medications, allergies, and procedures. These items may have been reported by the individuals themselves, based on their medical claims, or collected by health professionals, such as physicians, or nurses, in the physician's offices or in hospitals. The patients and the health professionals need to utilize the generally available medical knowledge, such as relationships among these items, in order to monitor and manage a patient's diagnosis over time.

SUMMARY OF THE INVENTION

In general, in one aspect, the invention features a method for processing a personal health record (PHR) including a plurality of events each having a time stamp. The method involves: creating a plurality of event-concept pairs by mapping each of the plurality of events in the PHR to a corresponding health concept; assigning to each of the plurality of event-concept pairs the time stamp of the event corresponding to the event-concept pair; identifying associations among the plurality of event-concept pairs; identifying an associative subset of event-concept pairs among the plurality of event-concept pairs; and linking a plurality of members of the associative subset of event-concept pairs to form a thread, wherein the thread presents a relationship among the plurality of members of the associative subset of event-concept pairs.

Other embodiments include one or more of the following features. Creating a plurality of event-concept pairs includes referencing a database. Identifying associations among the plurality of event-concept pairs includes referencing a database. The database stores a plurality of health concepts and a plurality of associations among the plurality of health concepts. Identifying an associative subset includes identifying a specific health concept and identifying a subset of the plurality of event-concept pairs wherein each member of the associative subset is at least associated with the specific health concept or associated with another event-concept pair in the associative subset. Identifying a specific health concept includes receiving an identification of the specific health concept from an external source. Linking members of the associative subset includes forming one or more sub-threads by selecting each member of the plurality of the members of the associative subset and linking the selected member to another member of the plurality of the members of the associative subset, if the selected member is associated with the another member, and further linking the one or more sub-threads thus formed chronologically to form the thread. The method also involves graphically presenting the thread to a user and finding a desired event-concept pair in the PHR, the desired event-concept pair satisfying an event-condition. The event-condition is to be associated with a specific health concept.

In general, in another aspect, the invention features another method for processing a plurality of personal health records (PHRs), each personal health record (PHR) of the plurality of PHRs including a plurality of events each having a time stamp. The method involves: processing each PHR of the plurality of PHRs, including: creating a plurality of event-concept pairs by mapping each of the plurality of events in the corresponding PHR to a corresponding health concept, assigning to each of the plurality of event-concept pairs the time stamp of the event corresponding to the event-concept pair, identifying associations among the plurality of event-concept pairs, identifying an associative subset of event-concept pairs among the plurality of event-concept pairs, and identifying a desired event-concept pair in the associative subset; and finding an aggregate result among the plurality of desired even-concept pairs corresponding to the plurality of PHRs.

Other embodiments include one or more of the following features. Identifying a desired event-concept pair in the associative subset includes identifying a member of the associative subset belonging to a specific heath-concept category. Processing each PHR of the plurality of PHRs further includes identifying a second event-concept pair associated with the desired event-concept pair, and finding a relationship corresponding to the desired event-concept pair and the second event-concept pair, and wherein finding an aggregate result includes aggregating the plurality of relationships corresponding to the plurality of PHRs. The relationship is a difference between the time stamp of the desired event-concept and the time stamp of the second event concept. The relationship is to determine whether the second event-concept satisfies a medical criteria. The aggregate result is an average of a value corresponding to each desired event-concept or the aggregate result is one of the total number of the desired event-concepts or the relative number of the desired event-concepts.

In general, in another aspect, the invention features a computer program product, residing on a computer-readable medium, for use in processing a personal health record (PHR) including a plurality of events each having a time stamp. The computer program product includes instructions for causing a computer to: create a plurality of event-concept pairs by mapping each of the plurality of events in the PHR to a corresponding health concept; assign to each of the plurality of event-concept pairs the time stamp of the event corresponding to the event-concept pair; identify associations among the plurality of event-concept pairs; identify an associative subset of event-concept pairs among the plurality of event-concept pairs; and link a plurality of members of the associative subset of event-concept pairs to form a thread, wherein the thread presents a relationship among the plurality of members of the associative subset of event-concept pairs.

In general, in still aspect, the features another computer program product, residing on a computer-readable medium, for use in processing a plurality of personal health records (PHRs), each personal health record (PHR) of the plurality of PHRs including a plurality of events each having a time stamp. The computer program product includes instructions for causing a computer to: process each PHR of the plurality of PHRs, including: create a plurality of event-concept pairs by mapping each of the plurality of events in the corresponding PHR to a corresponding health concept, assign to each of the plurality of event-concept pairs the time stamp of the event corresponding to the event-concept pair, identify associations among the plurality of event-concept pairs, identify an associative subset of event-concept pairs among the plurality of event-concept pairs, and identify a desired event-concept pair in the associative subset; and find an aggregate result among the plurality of desired even-concept pairs corresponding to the plurality of PHRs.

In general, in yet another aspect, the invention features a system for processing a personal health record (PHR) including a plurality of events each having a time stamp. The system includes: a mapper for creating a plurality of event-concept pairs by mapping each event of the plurality of events in the PHR to a corresponding health concept, for assigning to each of the plurality of event-concept pairs the time stamp of the event of that event-concept pair, and for identifying associations among the plurality of event-concept pairs; and a threader for identifying an associative subset of event-concept pairs among the plurality of event-concept pairs, and for linking a plurality of members of the associative subset of event-concept pairs to form a thread, wherein the thread presents a relationship among the plurality of members of the associative subset of event-concept pairs.

BRIEF DESCRIPTION OF THE DRAWINGS

FIG. 2 shows a list of a small subset of health concepts.

FIG. 3 shows an exemplary set of association types.

FIG. 9 shows a summary flow chart of the overall steps for generating a

DETAILED DESCRIPTION

Disclosed herein is a system called a threading system, and the associated method, which applies the latest medical knowledge to process health records of individuals. The threading system uses some of the medical information stored in a structured database to organize each individual's health record into subsets of clinically related events. The threading system presents each subset as a thread of events that are sorted by time and also connected based on their clinical relationship. Patients or their health providers can benefit from such system by being able to view the health record in an organized way—for example, to see the thread of all events relevant to a specific condition. The threading system further enables a user to search an individual's health record for a specific event or for all events that are clinically related to a specific medical concept.

The threading system can also find qualitative or quantitative relations among events in each health record, and aggregate those relations for multiple individuals (for instance, all patients within a population group). Medical researchers can use these aggregate results to derive clinical relationships, such as relationships between medications and side effects. Threading is different from other known techniques in the industry, like the "episodic grouping" technique. Episodic grouping associates items based solely on the episodes of care. Threading, on the other hand, groups the events based on the clinical reality of the patient over time and is independent of the number of times, if any, that the patient encounters the health care system.

Figure 1:
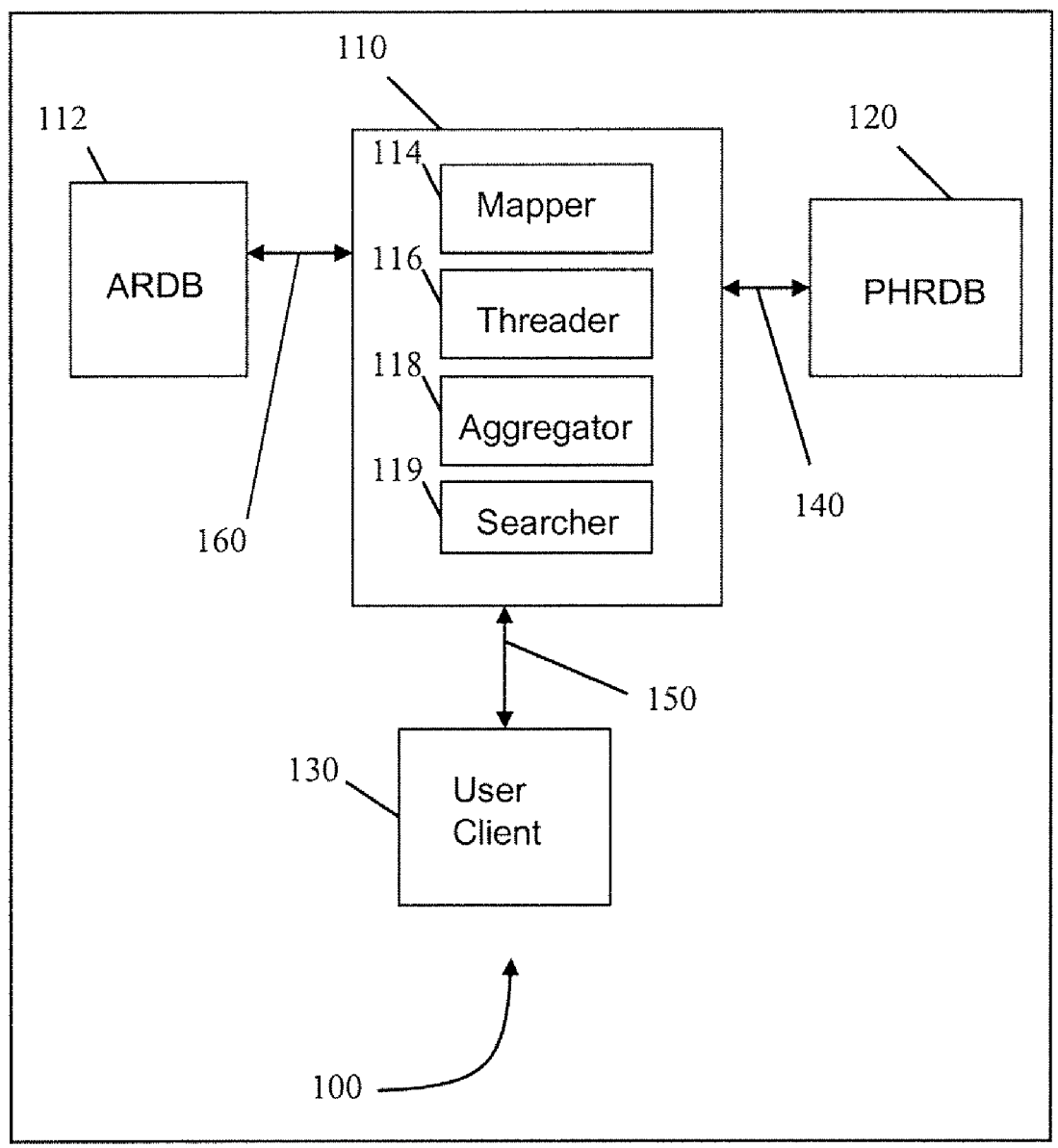
FIG. 1 is a block diagram of an exemplary system which implements the threading system.

FIG. 1 is a block diagram of an exemplary system 100 which implements threading for personal health records. System 100 includes a threading system 110, an associative relations database (ARDB) 112, a personal health record database (PHRDB) 120, a user client 130, and intercommunication channels 140, 150, and 160.

Threading system 110 contains various modules including a mapper 114, a threader 116, an aggregator 118, and a searcher 119. ARDB 112 is a database which stores the medical information and PHRDB 120 is a database which stores personal health records. These databases are for example created and populated by health professionals. Mapper 114, threader 116, aggregator 118, and searcher 119 are implemented as software modules or programs running on a computer such as the one shown in FIG. 11. Mapper 114 maps some of the events in each personal health record (PHR) to some of the medical concepts in the ARDB. Threader 116 uses the mapped events to generate for each PHR the threads of clinically related events. Aggregator 118 aggregates results from multiple PHRs to derive information used for example by the medical researchers. Searcher 119 searches within a PHR to find a specific event or events that are medically related to a specific medical concept. The ARDB, the mapper, the threader, the aggregator, and the searcher are discussed in greater detail below.

PHRDB 120 may reside in a database on a database server. User client 130 is a system, for example, implemented by a computer, through which a user interacts with the threading system. The user client can access the information provided by the threading system via a web browser. Alternatively, the user client can access the threading system via a threading interface running as a local program on the user client. Through user client 130 the user sends the threading system requests for analyzing a PHR or finding a thread and receives the output, for example a thread or an aggregate result.

Threading system 110 uses some of the medical knowledge available in ARDB database 112. ARDB 112 includes the medical items commonly found in the health records in the form of health concepts. Health concepts codify and unify the conceptual idea of each medical item, regardless of how that concept may be referred to in various systems—such as electronic records or billing systems—and regardless of which terms might be used to describe that concept—such as high blood pressure used by laypeople or hypertension used by health professionals.

Table 200 in FIG. 2 shows an exemplary list of a small subset of health concepts. Each row in FIG. 2 represents a health concept. Each entry in the first column is a clinical term. The second column includes a commonly used lay term corresponding to each clinical term. The third column shows the single concept unique identifier (CUI) for the listed clinical term. Each CUI is the code representing the specific idea or concept in health care which corresponds to the health concept. CUIs create a standard for referencing and using medical terms and enable different medical applications to communicate and work with each other. For example, as shown in the last row of Table 200, the condition commonly known as Sugar Disease is clinically termed Diabetes Mellitus and has the CUI value 00011849. While each health concept has a unique CUI, it may be associated with more than one lay term.

The ARDB organizes the health concepts into different categories. Examples of categories for health concepts include medical tests, diseases, symptoms, diagnoses, medications, and treatments. Each health concept can belong to one or more health concept categories. For instance, the health concept "Adrenalin-Test" in FIG. 2 belongs to the medical test category, and the health concept "Diabetes Mellitus" belongs to the disease category.

The ARDB also uses the latest medical knowledge to define different types of associations among the stored health concepts. One type of association between two health concepts is a taxonomic or parent-child association. A parent-child association relates two health concepts within the same category—e.g. two diseases or two medications—and indicates that one of the two concepts, the child, is an instance of the other concept, the parent. In other words, the parent represents a generic set, and the child is one specific member of that generic set. For example, heart disease is a member of the generic set of diseases called the disorder of blood vessels of thorax. So the health concept "Heart Disease" is a child of the health concept "Disorder of Blood Vessels of Thorax." On the other hand, heart disease itself represents a set of diseases which for example includes acute heart disease, and acute/subacute carditis. Thus the concept "Heart Disease" itself is the parent of the health concepts "Acute Heart Disease" and "Acute/subacute Carditis." In general a health concept can have more than one parent or more than one child. Taxonomic associations also exist between concepts in categories other than diseases. For instance, two different medications, or two different treatments can be associated by a parent-child association.

In addition to taxonomic associations, the ARDB defines other types of associations between health concepts. Unlike taxonomic associations, some associations associate two health concepts that belong to two different categories. As an example, the ARDB associates a disease with a symptom of that disease, or a treatment with a medication used in that treatment.

Table 300 in FIG. 3 shows an exemplary list of thirteen types of associations defined by the ARDB. Each association type has an identification (ID) listed in the first column, and a name representing the association, listed in the second column. For each association type, the third column lists the category pairs that can be associated by that association type. For example, the taxonomic association type is shown in the first row, with an ID equal to 1. As shown in the second and third columns, the taxonomic association is named an "Is_A" type (the child "is a" parent), and it can exist between two different diseases or two different medications or, in general, two concepts belonging to the same category. As a second example, shown in the second row of Table 300, an association of the type "is_treatment_for," with an ID equal to 2, can associate a medication concept with a disease concept. So this type of association exists between a medication and a disease, whenever that medication is known as a treatment for that disease. Some association types may associate more than one category pair. For example, the association "is_prevented_by," on row 11, may associate a symptom with a medication, to indicate that the symptom is known to be prevented by that medication. The same association, "is_prevented_by," may also associate a disease with a treatment, to indicate that the disease is known to be prevented by that treatment.

The threading system 110 uses the information in ARDB 112 to organize the personal health records of individuals. Each PHR contains information regarding an individual's health history. Each PHR can include different medical events in that history, such as observed symptoms, medical diagnoses, taken medications, performed operations, and treatments. Typically, each event is also stamped with the time that event occurred. A health provider may identify an event as a health concept and enter the CUI of that health concept into the PHR. Alternatively a health provider may identify an event with a lay term and enter the lay term into the PHR. In each PHR some of the events may be related to each other, for example by being associated with the same illness. Using the information in the ARDB, the threading system identifies and separately presents each group of events that are related.

Threading system 110 includes mapper 114, which maps the information in the PHR to the medical knowledge in the ARDB 112. For each medical event in the PHR, the mapper searches through the ARDB to find a health concept corresponding to that medical event, and, if it finds one, the mapper maps the medical event to that health concept. For those medical events that are entered into the PHR using their CUI, the corresponding health concept is the health concept with the same CUI. For medical events that are entered into the PHR using their lay term, the mapper utilizes mapping tables similar to that shown in FIG. 2 to find the health concept corresponding to that lay term. The result, called an event-concept pair for that event, carries the information in its event and in the corresponding health concept, including the time stamp of the event. For instance, a PHR may contain an event indicating that on a specific date the patient's symptoms were diagnosed as type two diabetes mellitus. The mapper will map this event to the concept "Diagnosis: Type 2 Diabetes Mellitus" and create an event-concept pair, with the time stamp of the event. An event-concept pair (or its event) also carries the association relationship properties of the corresponding health concept. That is, an event-concept pair (or its event) is considered to be associated with another event-concept pair (or its event) or associated with a health concept, when the corresponding health concepts are associated with each other. Going forward, whenever there is no cause for confusion, the term "event" is used for an "event-concept pair".

In order to further organize the PHR and to generate threads, threading system 110 includes threader 116. Threader 116 first uses the associations stored in the ARDB and the event-concept pairs created by the mapper, and generates one or more associative subsets. Each associative subset is a subset of all the events in the PHR in which each event is either associated with a specific 'header' health concept (e.g. a condition or a diagnosis) or associated with another event belonging to that subset. One method by which the threader finds the header concepts is by searching in the PHR for events corresponding to conditions or diagnoses. Alternatively the user may select a health concept, like a diagnosis, a condition, or a medication, as a header concept, irrespective of whether there is or there is not a corresponding event in the PHR. To generate the associative subset related to a header concept, the threader then selects those events in the PHR that are either associated with the header concept or associated with another event already selected for the associative subset.

For instance, when a patient is diagnosed with diabetes, his diagnosis may be based on some symptoms or test results associated with diabetes. Subsequently, he may undergo some additional diabetes related medical tests, or receive some treatments or medications for diabetes. Each of these pieces of information—symptoms, diagnosis, tests, or treatments—is a medical event which, along with its time stamp, is entered into the patient's PHR. When the threading system operates on this PHR, the mapper will map each event to a health concept, creating an event-concept pair. The threader then groups the above listed events into one associative subset, since they are all associated with the health concept Diabetes. For this associative subset, Diabetes is the header concept. This patient's PHR may also contain other events that are not associated with diabetes, and instead are routine tests or examinations, or are associated with a different diagnosis and ailment. The threader will not put those events in the mentioned associative subset.

Figure 4:
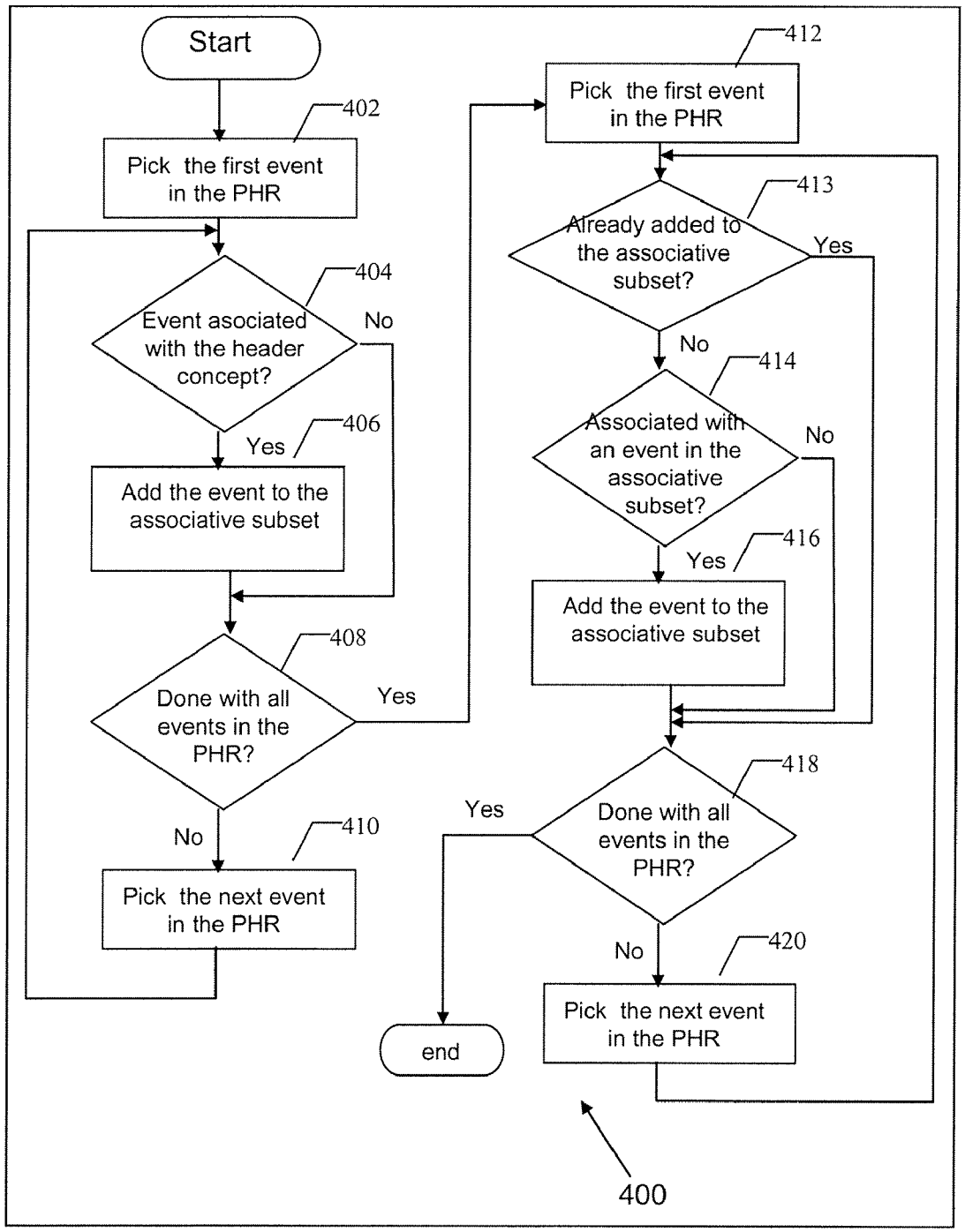
FIG. 4 shows a flow chart for generating an associative subset from the events in a PHR.

FIG. 4 shows a flow chart 400 illustrating an example of the steps taken by the threader in order to generate an associative subset from the events in a PHR. The threader first checks each event in the PHR (steps 402 and 410) and if the event is associated with the header concept (404), adds the event to the associative subset (406). Next, the threader once again checks each event in the PHR (steps 412 and 420) and if the event is not already added to the associative subset (413) and is associated with the an event already added to the associative subset (414), adds the event to the associative subset (416).

Figure 5:
FIG. 5 illustrates a "post visit summary" panel showing an associative subset.

FIG. 5 illustrates a "post visit summary" panel 500 as an exemplary interface in which an associative subset is shown. Panel 500 may be viewed by a patient using a user client 130. Panel 500 includes information related to one associative subset. The header concept for the associative subset is diagnosis 510, the health concept "Back Pain". This header concept is also an event in this PHR, since the patient has been diagnosed with back pain. Panel 500 shows different events from the PHR that all associated with "Back Pain". These events are organized under two health concept categories, "Medications" 520, and "Tests" 530. Under "Medications", two events are shown, which are the medications "Vicodin Tablets" 522 and "Mortin 800 mg Tablets" 524 prescribed during the last visit. Under "Tests", two other events are shown, the test "Back x-ray" 532 and the test "Uranalysis" 534, both performed during the last visit. In addition, panel 500 includes some other concepts, categorized under the health-concept category "Back Pain Treatment Options" 540, which are treatments associated with the header concept, "Back Pain", and extracted from the ARDB. These health-concepts are further grouped and presented under health concept sub-categories "Prescription Drug Treatments" 542, "Complementary Treatments" 544, and "Surgical Treatments" 546.

Figure 6:
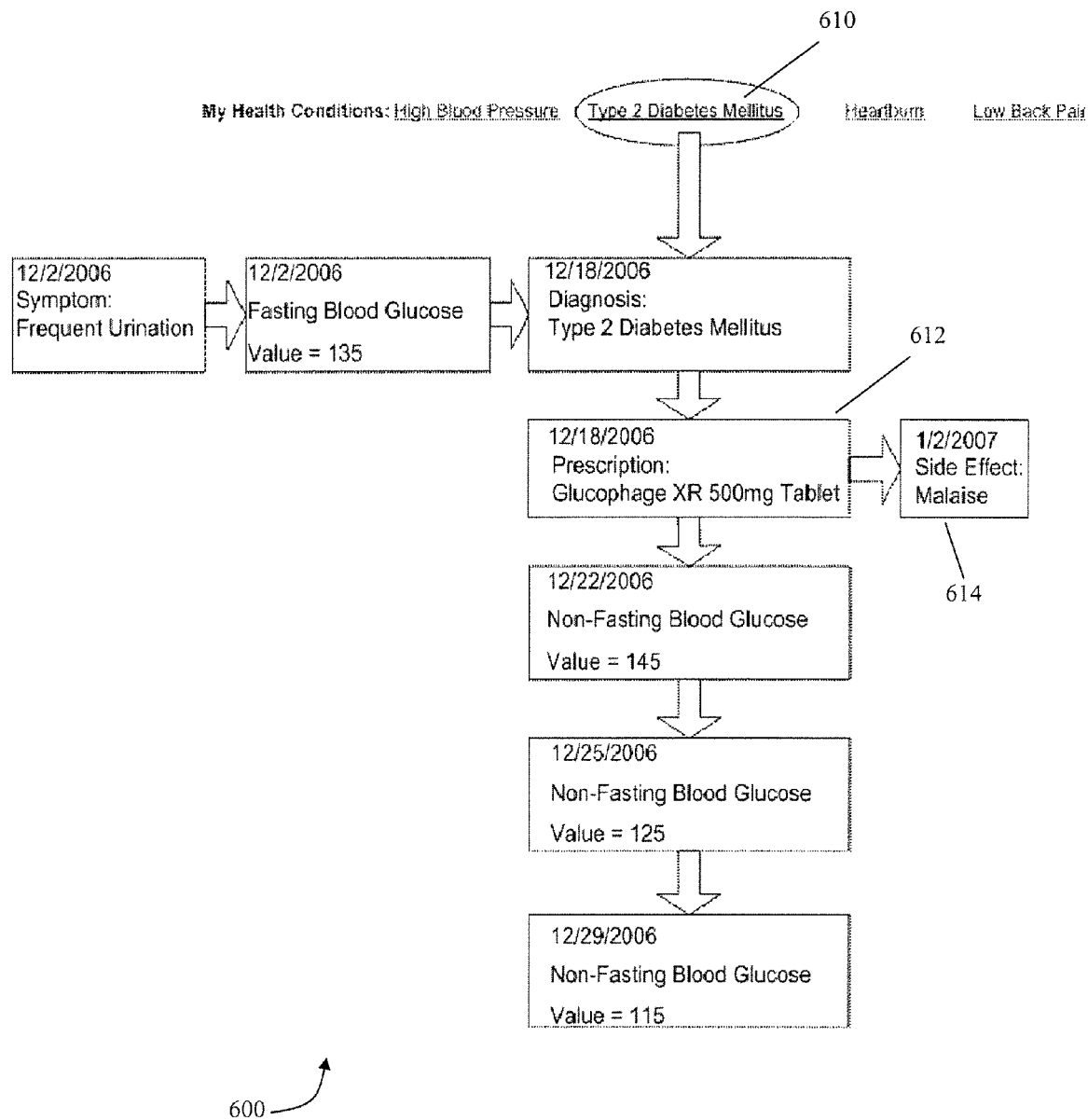
FIG. 6 shows a thread associated with a header concept.

The threader 116 then generates a thread from each associate subset. The threader sorts and connects events in an associative subset based on their time stamps or associations or both, and presents this connected set graphically as a chain of events, called an event thread. FIG. 6 shows an example of a thread, generated from an associative subset in a PHR. The user has selected for the header concept "Type 2 Diabetes Mellitus" 610, a diagnosis entered in the PHR for this patient. The thread includes the events in an associative subset of the PHR associated with this diagnosis. the thread starts with an event on Dec. 2, 2006, indicating that a symptom associated with type 2 Diabetes had been observed on that date. The subsequent events in the thread are a fasting blood test and its result on December 2, a diagnosis on December 18, a prescription of a medication associated with type 2 Diabetes on December 18, and three subsequent non-fasting blood tests and their results on December 22, December 25 and December 29, respectively. Also, the thread includes a side effect associated with (and thus connected to) the prescribed medication, observed on Jan. 2, 2007. Typically, the threading system builds the thread in FIG. 6 out of a larger set of events in the patient's PHR. This thread only includes events associated with header concept 610, Type 2 Diabetes Mellitus, and excludes events not associated with the header concept.

Figure 7:
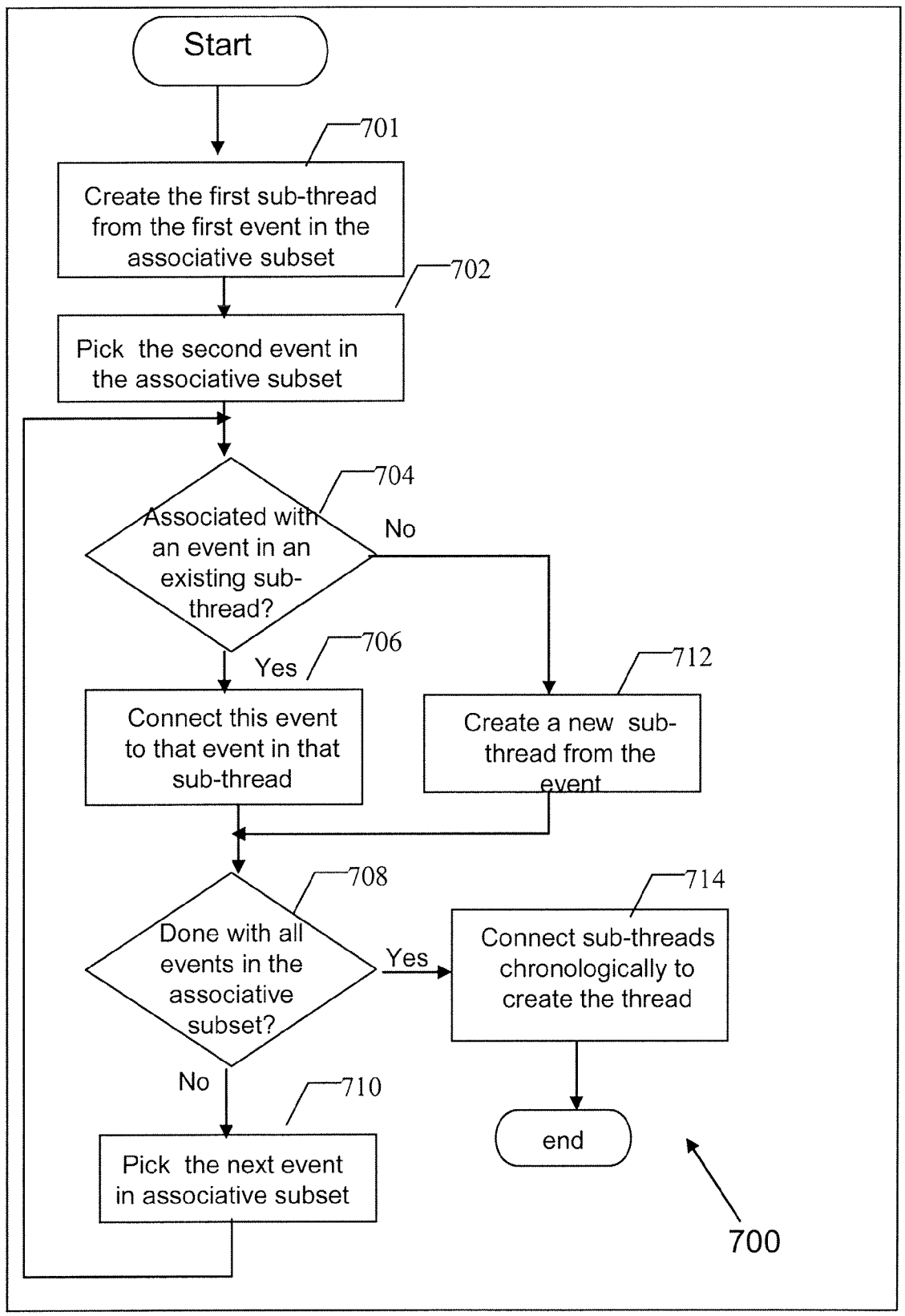
FIG. 7 shows a flow chart for generating a thread from an associative subset

FIG. 7 shows an exemplary flow chart of steps taken by the threader to generate a thread from an associative subset. The threader first creates sub-threads from each group of events that are associated with each other. To that end, the threader first creates the first sub-thread using the first event in the associative subset (701). The threader then picks the other events in the associative subset (702 and 710). If the picked event is associated with an event picked earlier (704), the threader connects the picked event to that earlier event and thus adds it to the sub-thread of the earlier event (706), otherwise, the threader will create a new sub-thread with the picked event (712). At the end of this process (708), the associative subset is partitioned into sub-threads, of which some might include one event and some may include more than one event. For example, in FIG. 6, the Side Effect 614 is associated with the Medication 612 and thus connected to that medication, and together they forms a two-event sub-thread. On the other hand, all other events in FIG. 6 are single event sub-threads, since they are only associated with the header concept and not with any other event in the associative subset. The threader then sorts these sub-threads chronologically, using the time stamp of the earliest event in each sub-thread and then connects each sub-thread to the next one in the sorted list, to form the thread (714).

The threading system enables a patient or a health professional to use the large volume of available medical knowledge in ARDB for analyzing an individual's PHR. When applying the threading system, the user can look into a PHR and view the historical progress of events that are medically related to a specific condition, diagnosis, treatment or, in general, a medical concept, independent of other medically unrelated events. As a result, a user can more easily make causal inferences or medical diagnoses and predictions. For example, for the thread shown in FIG. 6, a health professional may conclude that the patient's Malaise on Jan. 2, 2007 resulted from the medication that he started on Dec. 18, 2006, because Malaise is a symptom associated with that medication. It would likely be harder for the health professional to make the same inference by looking directly at the PHR, which includes a much larger set of not necessarily related events, sorted by time with no association connecting them.

Figure 8:
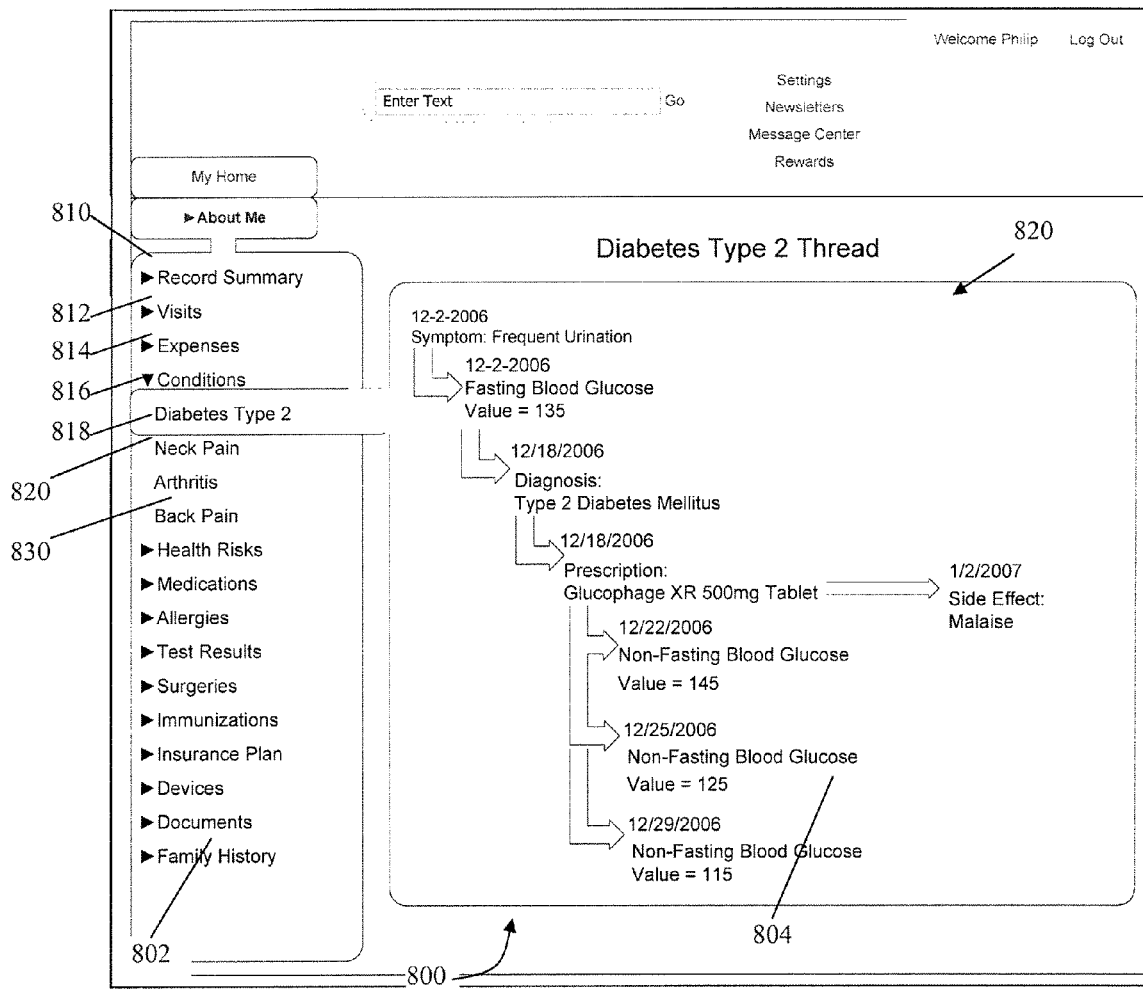
FIG. 8 shows a user interface through which the user can view the threads in a PHR.

FIG. 8 shows one example of a user interface 800 through which the user can select and view the threads in a PHR. On the left panel 802, the user can observe the list of conditions 810 present in the PHR. Once the user selects a condition as a header concept, in this example "Diabetes Type 2" 812, the threading system presents the thread 820 associated with the header concept in the right panel 804. The thread 820 is similar to the thread 600 discussed in relation with FIG. 6.

The threading system can group events in a PHR into separate event threads and present those threads to the user. The user can select a PHR and also optionally limit the events to be analyzed, for example, by selecting a time period. The threading system then divides the selected PHR into separate associative subsets and presents those subsets as separate threads. Through this feature, the threading system provides a systematic view of different medical problems or activities that may exist within a PHR. For example, in FIG. 8, subsets of events in the PHR are presented in different threads. The user can select each of the conditions "Diabetes Type 2" 812, "Neck Pain" 814, "Arthritis" 816, and "Back Pain" 818, to see the thread associated with that condition. The user can alternatively select a header concept from another category, e.g., the Health Risks 820, or the Allergies 830, to see the thread associated with the selected health risk or allergy.

Figure 9:
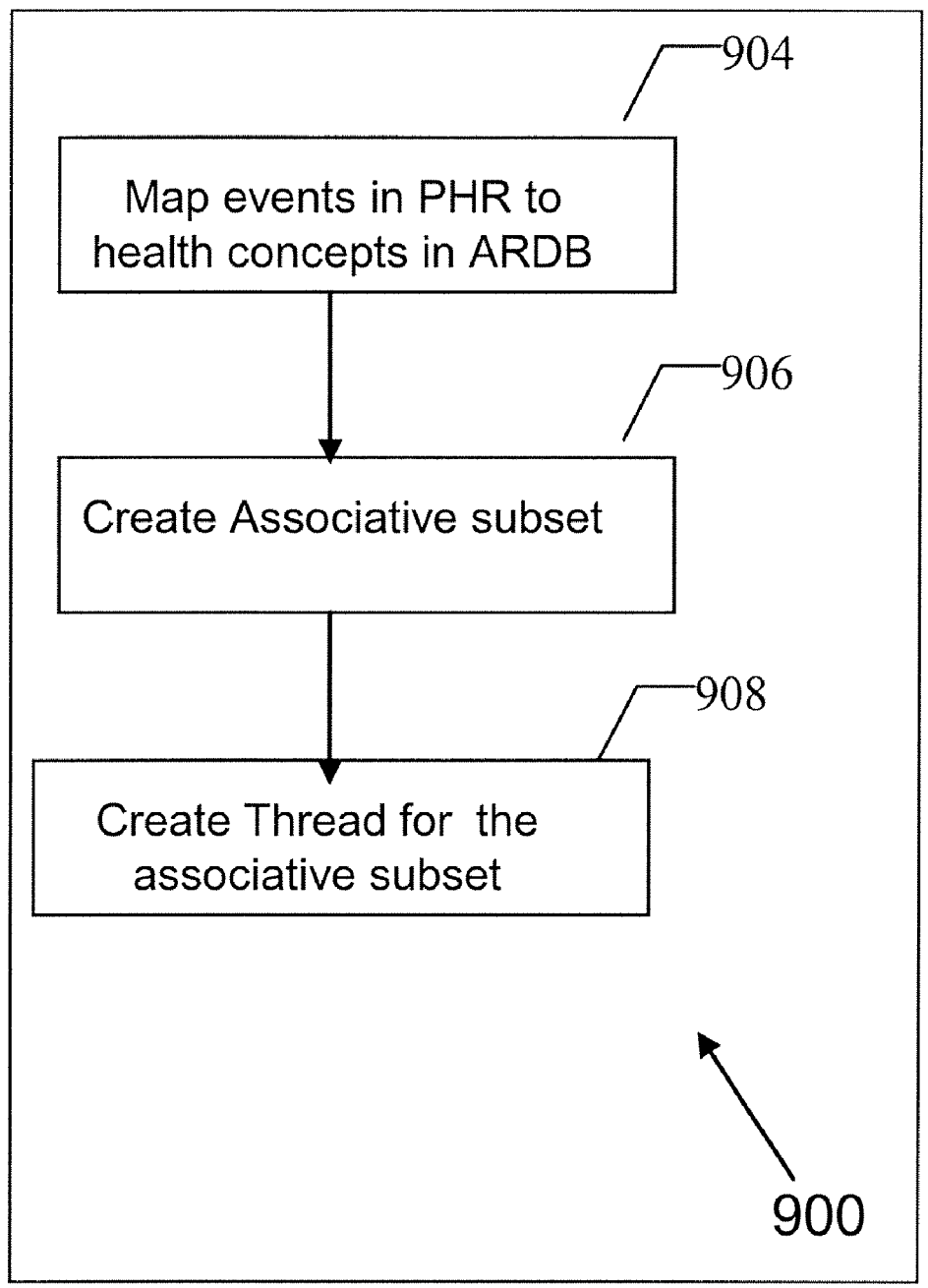

FIG. 9 shows a flow chart 900 which summarize the steps taken by the threading system to generate a thread, as detailed above. For each PHR, the mapper uses the information in ARDB and maps the events in the PHR to health concepts in ARDB to create event-concept pair (904). Then, the threader uses the event-concept pairs to generate associative subsets in each PHR (906). To generate an associative subset, the threader starts from a header concept provided by the user, or selected from events in the PHR or from a list of important health concepts (e.g., conditions). The threader then generates a thread from an associative subset (908).

To create the event-concept pairs in step 904, the threading system uses either a dynamic mapper or a static mapper. The dynamic mapper creates the event-concept pairs after a user submits a selection of a PHR and a header concept. The dynamic mapper then scans the PHR and, using the ARDB, creates the event-concept pairs for the events in the PHR. The dynamic mapper also finds and stores associations among those event-concept pairs. The dynamic mapper creates the event-concept pairs and the associations for all events in the PHR or for a subset of those events, e.g., those that are relevant to the request. The threader then uses these event-concept pairs and associations to generate and present the requested thread.

The static mapper, on the other hand, creates the event-concept pairs independent of any specific request and stores the event-concept pairs as static snapshots for future use. The static mapper can be more efficient than a dynamic mapper for some uses, for instance, when a user repeatedly requests event threads associated with a specific disease. The static mapper scans one or more PHRs from the PHRDB 120, e.g. PHRs that are often selected. It creates and stores all or the relevant subset of event-concept pairs for each PHR as a snapshot of that PHR. In addition, the static mapper also finds and stores in the snapshot all or a subset of associations among the event-concept pairs within each PHR. It also stores associations between the event-concept pairs of each PHR and one or more header concepts, for instance header concepts that are often selected. Whenever a user submits a request, the threader uses these stored snapshots, if relevant to the request, readily to generate the requested thread, without having to recreate the event-concept pairs or the associations anew each time. A threading system with a static mapper can update the static snapshots by adding or removing event-concept pairs or associations based on updates in the person's health record or in the ARDB.

Figure 10A:
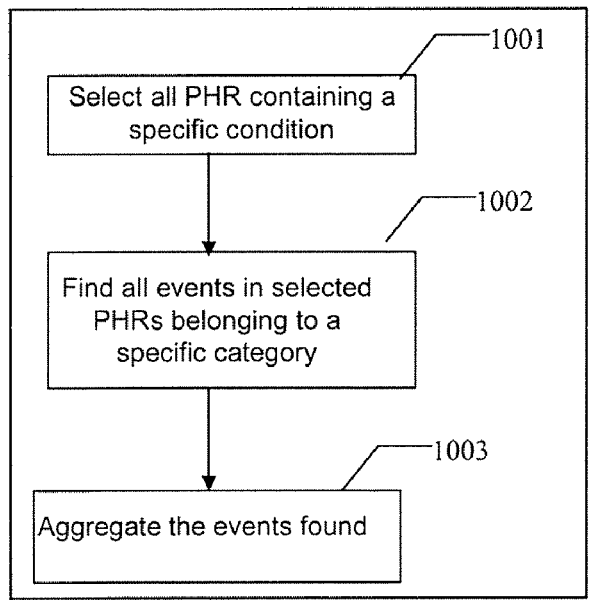
FIGS. 10A and 10B show flow charts for generating aggregate results.

Threading system 110 in the described embodiment includes aggregator 118 to automatically process the information in multiple PHRs from the PHRDB 120 and provide aggregate results. For instance, a researcher may be interested in analyzing the symptoms, common prescriptions, or side effects of treatments, for groups of patients diagnosed with the same condition, e.g. diabetes type 2. The researcher connects to the threading system's aggregator through a user-client 130. The researcher selects the condition, e.g., diabetes type 2, and a category as the subject for aggregation, e.g. symptoms or medication, or side effects of treatments. FIG. 10A depicts an exemplary set of steps taken by the aggregator 118 to respond to this request. First, aggregator automatically selects all PHRs in the PHRDB which include a thread of events associated with that specific condition (1001), e.g. all PHRs with a thread associated with diabetes type 2. The aggregator then searches within those threads in the selected PHRs to find all events belonging to the category selected by the researcher, e.g. symptoms, or prescriptions (1002). The aggregator then aggregates, e.g., sums up or averages, the occurrences of those found events belonging to the selected category (1003) and presents the result to the researcher through the user-client 130. In the example, the results for symptoms may indicate that 58% of patients presented initially with excessive urination, while 25% had excessive thirst, 22% had excessive hunger, and 20% had abdominal pain. The results for medication may indicate that 33% of patients use diet and exercise only, 25% use Metformin or Glucophage, while 20% are on Diabeta, and so on. The results for side effects may show that side effects are most common from Metformin, and that 15% of patients experience malaise, 5% experience muscle pain, etc.

Figure 10B:
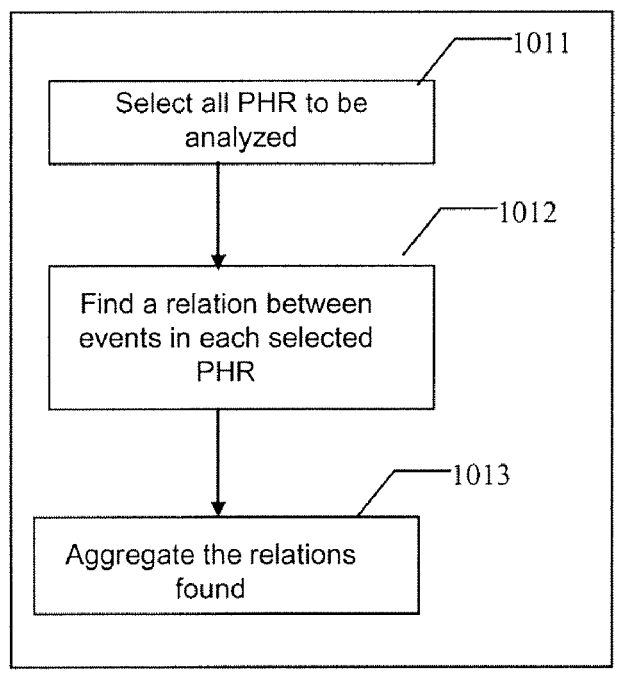

Alternatively, a researcher may be looking for an aggregate relationship between different health concepts, for example the time lapse between using a medication and observing its effects. FIG. 10B depicts an exemplary set of steps taken by the aggregator 118 to respond to this type of request. In this case, the aggregator finds the PHRs to be analyzed (1011). These PHR's may, for instance, belong to patients from a specific age group, or those diagnosed with a specific condition, or those who have undergone a specific treatment. The aggregator then processes the events in each PHR, finds the threads associated with the request, to derive a relation among its events (1012), for example, the time lapse between using a medication and observing its effects all within the threads associated with a specific condition. The aggregator then aggregates the relations found for different PHRs and provides the aggregate result (1013). The aggregate result can, for instance, indicate the average value of the time lapse mentioned above for multiple patients. The relation may be a qualitative relation, for example the causal relation between applying a medication and observing a side effect. The relation may also be a quantitative relation, for example the number of days it takes for a specific medication to reduce a biometric value, such as the blood pressure, by a specific amount. Health professionals and researchers can use the automatic analysis mechanism to efficiently analyze clinical data and derive medical information.

Medical researchers can also use the aggregation feature of the threading system to derive medical relationships between events for different groups in the population. For instance, a researcher may be interested in comparing the effectiveness of different medications in a specific age group diagnosed with high blood pressure. The aggregator can respond to this type of request utilizing threads in each PHR and following the process explained above. For instance, to respond to the above request, in the PHR of each patient, the aggregator find threads associated with high blood pressure condition, finds the different medications in those threads used to treat that condition along with measurements of some biometric values, such as blood pressure, over time. The aggregator then derives aggregate results based on threads in a group of PHRs which contain the same condition and medications, and also those biometric measurements. In each PHR, the aggregator first decides whether a medication was effective by checking whether the blood pressure dropped below some acceptable level within a specific period of time. Then, the aggregator combines these results for PHRs of different groups of patients that differ by their age group, body mass index, or otherwise, and derive aggregate results for each group. One of these results, for example, may say that for men between the ages of 40 and 50 who have a body mass index of between 25 and 30 and who have poorly controlled essential hypertension, the drug Monopril seems to be twice as effective as the other drug, Diovan, in helping the patient achieve control of his high blood pressure with a minimum number of side effects. A different analysis may focus on the association between side effects and medications and, for instance, find that 58% of diabetics who started Metformin were diagnosed with a urinary tract infection. Another analysis may focus on the association between blood pressure and treatments, and may for example conclude that 28% of heart disease patients lowered their blood pressure with diet and exercise alone, while 50% required a beta blocker medication.

Threading system 110 in the described embodiment includes searcher 119 which enables the user to search within a PHR for the occurrence of a specific health concept or all health concepts associated with a specific health concept, or all health concepts belonging to a specific health category. In performing this concept based search, the user selects a PHR and a header concept. The searcher 119 searches the PHR and, using either a dynamic mapper or a static snapshot of the PHR, finds all events associated with the header concept. Alternatively, the user may select a PHR and a health category. The searcher then searches the PHR for all threads containing events within the selected health category, and selects events in those threads belonging to the category. For instance, a user may search for "allergies" in his own PHR. In response, the threading system returns all of his doctor visits for allergies and their diagnoses of allergies, along with the date, and the treating provider. In addition, the threading system can return some other events associated with allergies, which could include the patient's allergy symptoms, his prescriptions for Allegro, and his allergy testing results.

Referring back to FIG. 1, any two or all three of the threading system 110, the PHRDB 120, and the user client 130 may reside on the same computer located in the healthcare facility. In this case, the communication channels 140 or 150 are for example communication busses inside the computer. Alternatively, these three may reside on different computers located in the healthcare facility or in different places. The user client 130 may alternatively reside on a computer in the patient's home or the health provider's office. In this case the communication channels 140 or 150 are for example, internet communication channels between the computers. Further, the ARDB 112 and the modules 114, 116, 118, and 119 may all reside on one computer, or different subsets of them may reside on different computers which communicate with each other through internet or through communication busses between those computers. The ARDB or PHRDB are stored on a storage system and can be of any format capable of containing and presenting the data in ARDB or PHRDB.

Health professionals or organizations can create ARDB 112 once, based on the existing medical knowledge, and then can update ARDB by adding or removing a concept or an association, for example because of a new medical discovery. Every time ARDB 112 is updated, threading system 110 can use the updated ARDB to create new event-concept pairs, associations, and threads.

Figure 11:
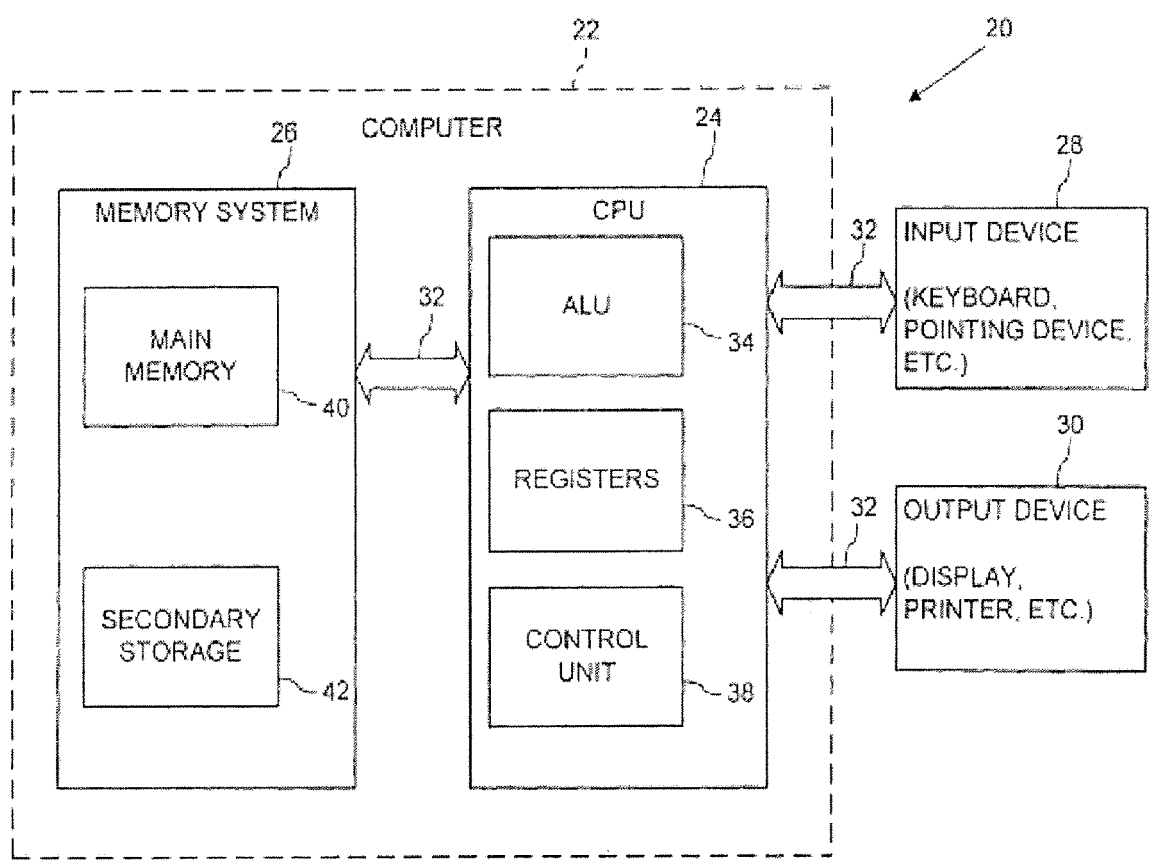
FIG. 11 illustrates an exemplary computer system that implements the threading system

FIG. 11 illustrates an exemplary computer system that can execute the software modules or programs contained in the threading system, i.e., the mapper, the threader, the aggregator and the searcher. Such a computer can also store each of the databases ARDB and PHRDB in its storage and provide their data to the modules or other users. In addition, such a computer can run the user client 130 which provides the interface for the user to interact with the threading system 110 and presents to the user the results from the threading system.

In FIG. 11, the computer system 20 includes a computer 22 which comprises at least one high speed processing unit (CPU) 24 a memory system 26. The computer system also includes an input device 28, and an output device 30. These elements are interconnected by at least one bus structure 32.

The CPU 24 includes an ALU 34 for performing computations, a collection of registers 36 for temporary storage of data and instructions, and a control unit 38 for controlling operation of the system 20. The memory system 26 includes high-speed main memory 40 in the form of a medium such as random access memory (RAM) and read only memory (ROM) semiconductor devices, and secondary storage 42 in the form of long term storage mediums such as floppy disks, hard disks, tape, CD-ROM, flash memory, etc. and other devices that store data using electrical, magnetic, optical or other recording media. The main memory 40 also can include video display memory for displaying images through a display device. The input device 28 can comprise a keyboard, a mouse, a physical transducer (e.g., a microphone), etc. The output device 30 can comprise a display, a printer, a transducer (e.g., a speaker), etc. Some devices, such as a network interface or a modem, can be used as input and/or output devices.

Other embodiments are within the following claims.

The invention claimed is:

1. A computer-implemented method for processing a personal health record (PHR) including a plurality of events each having a time stamp, the method comprising:
    creating a plurality of event-concept pairs by mapping each of the plurality of events in the PHR to a corresponding health concept among a plurality of health concepts;
    assigning to each of the plurality of event-concept pairs the time stamp of the event corresponding to the event-concept pair;
    identifying associations among the plurality of event-concept pairs, wherein the plurality of health concepts are categorized into a plurality of categories, wherein identifying associations involves referencing a database of stored information specifying associations between health concepts among the plurality of health concepts, wherein at least some of the specified associations are between health concepts that are in different categories in the plurality of categories, and wherein the plurality of categories are medical tests, diseases, symptoms, medications, and treatments;
    identifying an associative subset of event-concept pairs among the plurality of event-concept pairs, wherein the associative subset includes those events in the PHR that are either associated with a header concept or are associated with another event within the associative subset, and wherein the associated subset includes health concepts that are in different categories of the plurality of categories; and
    linking a plurality of members of the associative subset of event-concept pairs to form a thread, wherein the thread presents a relationship among the plurality of members of the associative subset of event-concept pairs,
    wherein creating, assigning, identifying associations, and linking are performed by a computer system.

2. The method of claim 1, wherein creating a plurality of event-concept pairs includes referencing a database that stores a plurality of health concepts.

3. The method of claim 1, wherein identifying an associative subset includes identifying a specific health concept and identifying a subset of the plurality of event-concept pairs wherein each member of the associative subset is at least associated with the specific health concept or associated with another event-concept pair in the associative subset.

4. The method of claim 3, wherein identifying a specific health concept includes receiving an identification of the specific health concept from an external source.

5. The method of claim 1, wherein linking members of the associative subset includes forming one or more sub-threads by selecting each member of the plurality of the members of the associative subset and linking the selected member to another member of the plurality of the members of the associative subset, if the selected member is associated with the another member, and further linking the one or more sub-threads thus formed chronologically to form the thread.

6. The method of claim 1, further comprising the step of graphically presenting the thread to a user.

7. The method of claim 1, further comprising the step of finding a desired event-concept pair in the PHR, the desired event-concept pair satisfying an event-condition.

8. The method of claim 7, wherein the event-condition is to be associated with a specific health concept.

9. A computer-implemented method for processing a plurality of personal health records (PHRs), each personal health record (PHR) of the plurality of PHRs including a plurality of events each having a time stamp, the method comprising:
  processing each PHR of the plurality of PHRs, including:
    creating a plurality of event-concept pairs by mapping each of the plurality of events in the corresponding PHR to a corresponding health concept among a plurality of health concepts,
    assigning to each of the plurality of event-concept pairs the time stamp of the event corresponding to the event-concept pair, wherein the plurality of health concepts are categorized into a plurality of categories,
    identifying associations among the plurality of event-concept pairs, wherein identifying associations involves referencing a database of stored information specifying associations between health concepts among the plurality of health concepts, wherein at least some of the specified associations are between health concepts that are in different categories in the plurality of categories, and wherein the plurality of categories are medical tests, diseases, symptoms, medications, and treatments,
    identifying an associative subset of event-concept pairs among the plurality of event-concept pairs, wherein the associative subset includes those events in the PHR that are either associated with a header concept or are associated with another event within the associative subset, and wherein the associated subset includes health concepts that are in different categories of the plurality of categories, and
    identifying a desired event-concept pair in the associative subset; and
      finding an aggregate result among the plurality of desired event-concept pairs corresponding to the plurality of PHRs,
  wherein processing and finding an aggregate result are performed by a computer system.

10. The method of claim 9, wherein identifying a desired event-concept pair in the associative subset includes identifying a member of the associative subset belonging to a specific heath-concept category.

11. The method of claim 9, wherein processing each PHR of the plurality of PHRs further includes identifying a second event-concept pair associated with the desired event-concept pair, and finding a relationship corresponding to the desired event-concept pair and the second event-concept pair, and wherein finding an aggregate result includes aggregating the plurality of relationships corresponding to the plurality of PHRs.

12. The method of claim 11, wherein the relationship is a difference between the time stamp of the desired event-concept and the time stamp of the second event concept.

13. The method of claim 11, wherein the relationship is to determine whether the second event-concept satisfies a medical criteria.

14. The method of claim 9, wherein the aggregate results is one of an average of a value corresponding to each desired event-concept, a total number of the desired event-concepts, or a relative number of the desired event-concepts.

15. A computer program product, residing on a physical computer-readable medium, for use in processing a personal health record (PHR) including a plurality of events each having a time stamp, the computer program product comprising instructions for causing a computer system to:
  create a plurality of event-concept pairs by mapping each of the plurality of events in the PHR to a corresponding health concept among a plurality of health concepts;
  assign to each of the plurality of event-concept pairs the time stamp of the event corresponding to the event-concept pair;
  identify associations among the plurality of event-concept pairs, wherein the plurality of health concepts are categorized into a plurality of categories, wherein identifying associations involves referencing a database of stored information specifying associations between health concepts among the plurality of health concepts, wherein at least some of the specified associations are between health concepts that are in different categories in the plurality of categories, and wherein the plurality of categories are medical tests, diseases, symptoms, medications, and treatments;
  identify an associative subset of event-concept pairs among the plurality of event-concept pairs, wherein the associative subset includes those events in the PHR that are either associated with a header concept or are associated with another event within the associative subset, and wherein the associated subset includes health concepts that are in different categories of the plurality of categories; and
  link a plurality of members of the associative subset of event-concept pairs to form a thread, wherein the thread presents a relationship among the plurality of members of the associative subset of event-concept pairs.

16. The computer program product of claim 15 further comprising instructions for causing a computer to of graphically present the thread to a user.

17. A computer program product, residing on a physical computer-readable medium, for use in processing a plurality of personal health records (PHRs), each personal health record (PHR) of the plurality of PHRs including a plurality of events each having a time stamp, the computer program product comprising instructions for causing a computer system to:
  process each PHR of the plurality of PHRs, including:
    create a plurality of event-concept pairs by mapping each of the plurality of events in the corresponding PHR to a corresponding health concept among a plurality of health concepts,
  assign to each of the plurality of event-concept pairs the time stamp of the event corresponding to the event-concept pair,
  identify associations among the plurality of event-concept pairs, wherein the plurality of health concepts are categorized into a plurality of categories, wherein identifying associations involves referencing a database of stored information specifying associations between health concepts among the plurality of health concepts, wherein at least some of the specified associations are between health concepts that are in different categories in the plurality of categories, and wherein the plurality of categories are medical tests, diseases, symptoms, medications, and treatments, identify an associative subset of event-concept pairs among the plurality of event-concept pairs, wherein the associative subset includes those events in the PHR that are either associated with a header concept or are associated with another event within the associative subset, and wherein the associated subset includes health concepts that are in different categories of the plurality of categories, and identify a desired event-concept pair in the associative subset; and find an aggregate result among the plurality of desired even-concept pairs corresponding to the plurality of PHRs.

18. A system for processing a personal health record (PHR) including a plurality of events each having a time stamp, the system comprising:

a mapper for creating a plurality of event-concept pairs by mapping each event of the plurality of events in the PHR to a corresponding health concept among a plurality of health concepts, for assigning to each of the plurality of event-concept pairs the time stamp of the event of that event-concept pair, and for identifying associations among the plurality of event-concept pairs, wherein the plurality of health concepts are categorized into a plurality of categories, wherein identifying associations involves referencing a database of stored information specifying associations between health concepts among the plurality of health concepts, wherein at least some of the specified associations are between health concepts that are in different categories in the plurality of categories, and wherein the plurality of categories are medical tests, diseases, symptoms, medications, and treatments; and a threader for identifying an associative subset of event-concept pairs among the plurality of event-concept pairs, wherein the associative subset includes those events in the PHR that are either associated with a header concept or are associated with another event within the associative subset and wherein the associated subset includes health concepts that are in different categories of the plurality of categories, and for linking a plurality of members of the associative subset of event-concept pairs to form a thread, wherein the thread presents a relationship among the plurality of members of the associative subset of event-concept pairs, and wherein the mapper and the threader are implemented in hardware.

19. The system of claim 18, wherein the mapper finds the corresponding health concept from a plurality of health concepts by referencing a database that stores a plurality of health concepts.

20. The system of claim 18, wherein the mapper identifies associations among the plurality of event-concept pairs by referencing a database that stores a plurality of health concepts and a plurality of associations among the plurality of health concepts.

21. The system of claim 18, wherein the threader identifies an associative subset by identifying a specific health concept and identifying a subset of the plurality of event-concept pairs wherein each member of the associative subset is at least associated with the specific health concept or associated with another event-concept pair in the associative subset.

22. The system of claim 18, further comprising a searcher for finding a desired event-concept pair in the PHR, the desired event-concept pair satisfying an event-condition.

23. The system of claim 22, wherein the event-condition is to be associated with a specific health concept.

24. A system for processing a plurality of personal health records (PHRs), each personal health record (PHR) of the plurality of PHRs including a plurality of events each having a time stamp, the system comprising:

a mapper for creating a plurality of event-concept pairs for each PHR of the plurality of PHRs, by mapping each event of the plurality of events in the corresponding PHR to a corresponding health concept among a plurality of health concepts, for assigning to each of the plurality of event-concept pairs the time stamp of the event of that event-concept pair, and for identifying associations among the plurality of event-concept pairs, wherein the plurality of health concepts are categorized into a plurality of categories, wherein identifying associations involves referencing a database of stored information specifying associations between health concepts among the plurality of health concepts, wherein at least some of the specified associations are between health concepts that are in different categories in the plurality of categories, and wherein the plurality of categories are medical tests, diseases, symptoms, medications, and treatments;

a threader for identifying an associative subset of event-concept pairs among the plurality of event-concept pairs for each PHR of the plurality of PHRs, wherein each associative subset includes those events in the PHR that are either associated with a header concept or are associated with another event within the associative subset and wherein the associated subset includes health concepts that are in different categories of the plurality of categories; and an aggregator for identifying a desired event-concept pair in the associative subset identified for each PHR, and for finding an aggregate result among the plurality of desired even-concept pairs corresponding to the plurality of PHRs, and wherein the mapper, the threader, and the aggregator are implemented in hardware.

25. The system of claim 24, wherein the aggregator processes each PHR of the plurality of PHRs by further identifying a second event-concept pair associated with the desired event-concept pair, and by finding a relationship corresponding to the desired event-concept pair and the second event-concept pair, and wherein the aggregator finds an aggregate result by aggregating the plurality of relationships corresponding to the plurality of PHRs.

26. The system of claim 25, wherein the relationship is a difference between the time stamp of the desired event-concept and the time stamp of the second event concept.

27. The system of claim 25, wherein the relationship is to determine whether the second event-concept satisfies a medical criteria.

28. The system of claim 24, wherein the aggregate results is an average of a value corresponding to each desired event-concept.

* * * * *

UNITED STATES PATENT AND TRADEMARK OFFICE
CERTIFICATE OF CORRECTION

PATENT NO.         : 8,380,530 B2  
APPLICATION NO.    : 12/025421  
DATED              : February 19, 2013  
INVENTOR(S)        : Phillip Marshall Page 1 of 1

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 916 days.

Signed and Sealed this
Second Day of June, 2015

Michelle K. Lee
*Director of the United States Patent and Trademark Office*